(12) United States Patent
Slater (10) Patent No.: US 12,236,804 B2
(45) Date of Patent: Feb. 25, 2025

(54) METHODS AND SYSTEMS FOR GRADUAL EXPOSURE TO A FEAR

(71) Applicants: UNIVERSITAT DE BARCELONA, Barcelona (ES); INSTITUCIÓ CATALANA DE RECERCA I ESTUDIS AVANÇATS, Barcelona (ES)

(72) Inventor: Mel Slater, Barcelona (ES)

(73) Assignees: UNIVERSITAT DE BARCELONA, Barcelona (ES); INSTITUCIÓ CATALANA DE RECERCA I ESTUDIS AVANÇATS, Barcelona (ES)

( * ) Notice: Subject to any disclaimer, the term of this patent is extended or adjusted under 35 U.S.C. 154(b) by 1059 days.

(21) Appl. No.: 17/057,083

(22) PCT Filed: May 22, 2019

(86) PCT No.: PCT/EP2019/063176
§ 371 (c)(1),
(2) Date: Nov. 19, 2020

(87) PCT Pub. No.: WO2019/224230
PCT Pub. Date: Nov. 28, 2019

(65) Prior Publication Data
US 2021/0312827 A1 Oct. 7, 2021

(30) Foreign Application Priority Data
May 23, 2018 (EP) .................................... 18382354

(51) Int. Cl.
*G09B 9/00* (2006.01)
*A61B 5/00* (2006.01)
(Continued)

(52) U.S. Cl.
CPC .............. *G09B 9/00* (2013.01); *A61B 5/0205* (2013.01); *A61B 5/024* (2013.01); *A61B 5/0816* (2013.01);
(Continued)

(58) Field of Classification Search
None
See application file for complete search history.

(56) References Cited

U.S. PATENT DOCUMENTS 6,012,926 A * 1/2000 Hodges ................. A61M 21/00
434/48
2010/0178639 A1* 7/2010 Kameyama ........... A61M 21/00
434/236

FOREIGN PATENT DOCUMENTS

WO WO 2017/021321 A1 2/2017

OTHER PUBLICATIONS

International Search Report and Written Opinion mailed Aug. 5, 2019 for International Application No. PCT/EP2019/063176, 11 pages.

* cited by examiner

*Primary Examiner* — James B Hull
(74) *Attorney, Agent, or Firm* — SQUIRE PATTON BOGGS (US) LLP (57) ABSTRACT

Methods for gradually exposing a subject to a fear comprising: adapting a virtual reality scenario to expose the subject to the fear by gradually transforming one or more of objects from a first state to a second state, the second state of the object provoking an increase of the fear, and wherein the transforming one or more of the objects take place only if the following two conditions are fulfilled: a time condition specifying an amount of time from the previous increase of fear, and the object is in a peripheral field of vision of the subject as derived from the orientation of the head mounted
(Continued)

device. A computer program and computing systems for gradually exposing a subject to a fear are also disclosed.

6 Claims, 8 Drawing Sheets

(51) Int. Cl.
*A61B 5/0205* (2006.01)
*A61B 5/024* (2006.01)
*A61B 5/08* (2006.01)
*G06F 3/01* (2006.01)
*G09B 19/04* (2006.01)

(52) U.S. Cl.
CPC ............ *A61B 5/4266* (2013.01); *A61B 5/741* (2013.01); *G06F 3/012* (2013.01); *G09B 19/04* (2013.01)

METHODS AND SYSTEMS FOR GRADUAL EXPOSURE TO A FEAR

CROSS-REFERENCE

The present application is a 35 USC 371 national phase filing of PCT/EP2019/063176 filed on May 22, 2019, which claims the benefit and priority of European patent application EP18382354.1 filed on May 23, 2018, both applications are incorporated herein by reference in their entirety.

The present disclosure relates to methods, systems and computer readable media for for gradually exposing a subject to a fear. More particularly, the present disclosure relates to such methods and systems based on the use of Virtual Reality.

BACKGROUND ART

A phobia is an irrational fear of an object, activity, or situation that leads to a compelling desire to avoid it e.g. fear of heights or fear of public speaking. Not only is there a wide variety of phobias, but any given type of fear may manifest itself differently, or to a different degree, in different persons. Therefore, treatment programs generally have to be tailored individually to specific patients. Nevertheless, certain generalities in regard to treatment programs can be made.

The most usual treatments and support for phobias comprise psychotherapy and/or medication. Prolonged use of medication however can produce unwanted side effects. A psychotherapy treatment program may be based on the "exposure theory". This theory espouses the view that patients suffering from a particular phobia can be treated to successfully manage that phobia by repeated exposure to the particular situation. For example, patients suffering from acrophobia (fear of heights) may be treated by exposure to heights. Elevators, balconies, building windows, bridges, and airplanes are environments in which a person suffering from fear of height may experience fear. Repeated exposure to such environments can help to reduce the fear or the effects that the fear has on a person's well-being. Although the degree of success varies from patient to patient, exposure therapy has been proven effective in many cases and controlled studies.

A more particular derivation of exposure therapy is referred to as "graded exposure therapy", whereby a patient is exposed to particular situations in gradations of gradual but increasing severity. For example, the above-commented acrophobic patient may be treated by leading the person to a first floor balcony. While this initially may result in relatively high levels of anxiety, it has been found that the anxiety level typically subsides after a patient has spent some time in the environment. Therefore, after the patient has spent some time on the first floor balcony, and has reached some level of comfort in that position, he/she may then be taken to a second floor balcony, and so on. In this way, the patient may gradually be moved to increased heights, allowing the anxiety level to subside at each level before continuing. Repeated sessions of treatment in this manner i.e. graded exposure have been found to successfully help patients in facing and managing phobias.

Similarly, a person who has a fear of speaking in public may first be asked to talk to an audience of one person, e.g. the therapist. In a next session, possibly a week later, the person may be asked to speak in front of two or three persons and so on.

However, such methods are not always effective in the short or in the long term, they are costly and time-consuming, and require the individual to be actively involved and proactive in order to make the most of the methods. Particularly, several therapy sessions may be needed along several days/weeks to treat the phobia. Additionally, in certain treatment environments such as an elevator or an airplane, the environment is not under patient or therapist control, often resulting in excessive levels of anxiety on the part of the patient, which may be counter-productive for the therapy.

In this respect, Virtual reality (VR) offers a variety of potential benefits for many aspects of treatment, and research. VR has the capacity to allow the creation and control of dynamic 3-dimensional environments, to provide extensive sensory feedback, plus ecologically valid stimulus in environments within which behavioural responding can be recorded and measured. Thus, VR offers increased flexibility in clinical assessment and therapeutic options that are not available with traditional methods. Instead of a person with fear of flying actually boarding a plane, a virtual environment of the plane may be created. The virtual reality can be under (complete) control of a therapist. It is possible to create specific scenarios and environments that are deemed suitable for an individual patient.

It is an object of the present disclosure to provide methods and systems for gradually exposing a subject to a fear that resolves some of the aforementioned problems.

SUMMARY

In a first aspect, a method for gradually exposing a subject to a fear is provided, wherein the subject wears a head mounted device for displaying a partially preprogrammed virtual reality scenario. The method comprises substantially continuously receiving from one or more sensors an orientation of the head mounted device of the subject, substantially continuously determining a video signal including one or more objects in the virtual reality scenario to be displayed on the head mounted device taking into account the received orientation of the head mounted device and sending the video signal to the head mounted device for visualization. The method further comprises: adapting the virtual reality scenario to expose the subject to the fear by gradually transforming one or more of the objects from a first state to a second state, the second state of the object aimed at provoking an increased anxiety because of the fear, and wherein the transforming one or more of the objects takes place only if the following two conditions are fulfilled: a time condition specifying an amount of time from the previous increase of fear has been fulfilled, and the object is in a peripheral field of vision of the subject as derived from the orientation of the head mounted device.

According to this aspect, a virtual treatment of a fear of a subject may result in an improved physiological and behavioral response, without the administration of medication and thus avoiding their side effects, and yielding a cost-effective and time saving alternative for the traditional therapy. Moreover, an extensive virtual treatment of the fear may be performed in a single session instead of the traditional therapy wherein several sessions over time may be needed.

A fully immersive virtual reality environment may be provided. Particularly, an immersive virtual reality environment refers to a computer-simulated environment with which a subject is able to interact. As the subject moves his/her head, the video signal reproduced on the head mounted display is adapted to the real-time orientation of the head mounted device so that a feeling of "being physically"

or perceptually within the environment is created. Therefore, the immersive virtual reality environment creates an illusion to the subject that he/she is in an artificially created environment which imitates the relationship between the subject and the surrounding environment.

During a treatment session, the subject wears the head mounted device for displaying a partially preprogrammed virtual reality scenario. The virtual reality scenario is adapted to gradually expose the subject to the fear by gradually and practically imperceptibly transforming one or more of the displayed objects from a first state to a second state. Particularly, in the second state, the objects are chosen in relation to the fear of the subject to cause increased anxiety.

In this respect, the subject's brain may continue to think that no fear can be associated to the objects due to the gradual transformation of such objects. Exposure therapy identifies the effects of the patient to the fear-induced stimulus and breaks response through measured exposure until habituation is achieved. The subject is thus trained on how to cope with the fear with the gradual exposure to the fear via the gradual transformation of the objects displayed in the preprogrammed virtual reality scenario e.g. in a single treatment session.

The adaptation of the virtual reality scenario by transforming of the objects from the first state to the second state (this state provoking an increase in the fear of the subject) is performed only if two conditions are fulfilled, namely if a time condition specifying an amount of time from the previous increase of fear is fulfilled, and if a condition that the object is in a peripheral field of vision of the subject as derived from the orientation of the head mounted device is fulfilled.

In some examples, the time condition is a variable amount of time depending on a perceived state of the subject. The time condition specifying an amount of time from the previous state may thus be set and adjusted based on the state of the subject. This way, the intensity of the exposure of the subject to the fear may be altered. For example, the rate at which the objects change from one state (which provokes less fear or anxiety in the subject) to another state (which provokes more fear or anxiety in the subject) may be varied by specifying a suitable amount of time from the previous increase of fear. The subject may thus be suitably exposed to the fear and the degree of immersion of the subject to the fear may be controlled.

The suitable time condition may be set up by e.g. a healthcare professional who may decide to increase or not the exposure of the subject. If the healthcare professional judges that the exposure of the subject to the fear should be increased then the amount of time from the previous state may be reduced. However, if he/she judges that the exposure the subject to the fear should be decreased then the amount of time from the previous state amount of time may be decreased.

In examples, one or more sensors configured to measure, for instance, the real breathing or heart rate of the subject may be provided. The amount of time may thus be automatically varied and controlled based on such measurements. Other parameters that might be measured include any parameter that can be directly or indirectly linked to anxiety or stress.

In some other examples, the time condition is simply a predetermined amount of time since the previous increase of fear.

Using this graded exposure to the fear, the subject is exposed to a particular fear that elicits an increased anxiety in a gradual or subtle way. After a suitable amount of time with continued exposure to the fear, the objects are transformed to a further state to change or intensify the fear at which the subject is exposed. This process is repeated through several gradations as a way of efficiently exposing patients to feared environments.

Moreover, the objects are in a peripheral field of vision of the subject as derived from the orientation of the head mounted device when they undergo the transformation. It has been found that an angle off the orientation of the head mounting display can be sufficiently out of the primary focus of attention or center of gaze of the subject such that the gradual transformation of the objects does not distract the subject and the subject may thus be practically unaware of the transformation.

The objects located in a peripheral field of vision of the subject as derived from the orientation of the head mounted device are in a form that may be seen by partial conscious observation of the subject but are not so obvious as to be distracting from the primary focus of attention. The gradual exposure to the fear then imposes its influence on the subconscious mind, thereby introducing the fear into the subconscious mind during other activities of the subject, namely while the subject is focused on the primary focus of attention.

The subconscious mind is known to take in information on a subconscious level without interfering with the conscious attention of the observer. In this manner, the subconscious mind of the subject is confronted with its fears but the subject does not notice it. The method may thus rely on "change blindness" (a perceptual phenomenon that occurs when a change in a visual stimulus is introduced and the subject does not notice it) as well.

The preprogrammed virtual reality scenario may be tailored to specific patient needs. In this respect, the virtual reality treatment may be much more efficient and cost effective for treating patients than actual exposure methods. That is, in connection with e.g. patients having a fear of public speaking, the emulated environment is much more cost effective than actually having to bring the subject to a real scenario with random people as an audience. Moreover, in examples, by staying within the confines of the therapist's office, patient confidentiality may be maintained. Additionally, unlike a real scenario, if it is clinically warranted, the exposure session may be immediately terminated. It is well appreciated that such an option is not available in a real-world exposure session. Moreover, the adaptation of the virtual reality scenario may be tailored as well for a specific patient. In some of the aforementioned examples, an increased exposure to fear may be established specifically when the subject is "ready" for it.

It is further noted that the preprogrammed virtual reality scenario to be displayed may be previously selected by e.g. a practitioner or the subject himself/herself from a module comprising a plurality of pre-preprogramed scenarios directed to overcome a particular fear. A library of scenarios might be established for a variety of fears.

In some examples, the method further comprises substantially continuously receiving from one or more sensors movements carried out by body parts of the subject, wherein the video signal includes an avatar of the subject in the virtual reality scenario, the avatar of the subject performing the movements carried out by body parts of the subject.

In this respect, as a subject moves his/her head, the video signal reproduced on the head mounted display is adapted to the real-time orientation of the head mounted display so that "ownership" of the avatar of the subject is achieved i.e. the subject's brain is cheated into thinking that the virtual body belongs to the subject.

The virtual reality scenario may thus enable participants to embody the virtual avatar of the subject. Patients may be endowed with life-sized virtual bodies that substitute their own body. The virtual body may be spatially coincident with the participant's real body, matching their posture and body movements, and it may be seen from a first person perspective. In some examples, the virtual avatar used to represent a subject may be selected from a library of available avatars. In other examples, a specific avatar based upon e.g. a body scan, photo or video footage may be created for a subject.

In another aspect, a computing system comprising a memory and a processor, wherein the memory stores computer program instructions executable by the processor is disclosed. The instructions may comprise the functionality to execute a method for gradually exposing a subject to a fear according to any of the examples disclosed herein.

In yet another aspect, a system for gradually exposing a subject to a fear may comprise a computing system as above, a head-mounted display configured to reproduce a video signal received from the computing system, and one or more sensors configured to measure an orientation of a head mounted display of the subject In some examples, the sensors configured to measure an orientation of a head mounted device may comprise accelerometers attached to, integrated in or coupled with the head mounted device. In other examples, the sensors may comprise video cameras. Software for object recognition and motion capture hardware can be used to determine movements of the subject and/or the head mounted device. In yet further examples, further sensors involving e.g. emitters and receivers, from which the position and orientation of the subject or the head mounted device may be derived from triangulation. In yet further examples, the sensors may include a geomagnetic field sensor integrated in the head mounted display.

In the examples disclosed herein, many different suitable head mounted devices could be used. For example, a Smartphone or tablet incorporated in a head mount may serve as the head mounted device or display.

In some examples, the system may further comprise headphones. The computing system in such cases may send suitable audio signals for reproduction by the headphones. Through the headphones, the subject may hear a real or manipulated voice talking about the fear of the subject. For instance, the subject/user may be questioned by a health care provided and encourage to speak about his/her fears.

In yet another aspect, a computer program comprising program instructions to carry out any of the methods for gradually exposing a subject to a fear herein explained is disclosed. The computer program product may be embodied on a computer readable medium and may comprise instructions to provoke that a controller device implements a method for gradually exposing a subject to a fear according to examples disclosed herein.

The computer program product may be embodied on a storage medium (for example, a CD-ROM, a DVD, a USB drive, on a computer memory or on a read-only memory) or carried on a carrier signal (for example, on an electrical or optical carrier signal).

The computer program may be in the form of source code, object code, a code intermediate source and object code such as in partially compiled form, or in any other form suitable for use in the implementation of the processes. The carrier may be any entity or device capable of carrying the computer program. Further, the carrier may be a transmissible carrier such as an electrical or optical signal, which may be conveyed via electrical or optical cable or by radio or other means.

When the computer program is embodied in a signal that may be conveyed directly by a cable or other device or means, the carrier may be constituted by such cable or other device or means.

Alternatively, the carrier may be an integrated circuit in which the computer program is embedded, the integrated circuit being adapted for performing, or for use in the performance of, the relevant methods.

DESCRIPTION OF THE DRAWINGS

Non-limiting examples of the present disclosure will be described in the following, with reference to the appended drawings, in which.

DETAILED DESCRIPTION

Figure 1:
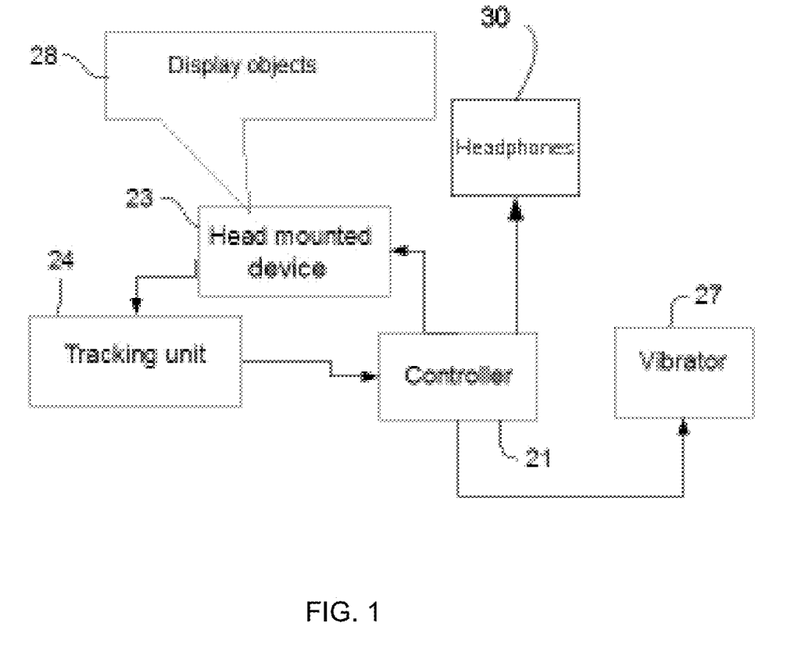
FIG. 1 illustrates a block diagram of an example of a system for gradually exposing a subject to a fear.

FIG. 1 illustrates a block diagram describing an example of a system for gradually exposing a subject to a fear. The system may comprise a computing system of controller 21 connected to a head mounted device 23, a tracking unit 24, and headphones 30. In this particular example, the system furthermore comprises a vibrator 27.

The head mounted device 23 (HMD) may take many suitable shapes and forms. As mentioned before, it may consist of a mobile phone or Smartphone or tablet arranged in some form of head mount. Notably, there is not necessarily a need for significant computing power in the HMD. The computing power may be provided in the actual HMD, but in some examples, the computing system may be physically separate from the HMD. The computing system in these cases may have a wireless connection with the HMD or may have a cable connection.

The head mounted device 23 may further comprise a screen. The screen may be flat or, alternatively, curved, either physically or optically, to extend to each side of the eyes and effectively cover the users peripheral vision.

The tracking unit 24 may include a plurality of sensors that in particular may determine the orientation and also the position of the head mounted device. From these sensors, the point of view and direction of view e.g. the center of gaze of the patient may be determined and this information is used to calculate the appropriate video signal corresponding to what the patient would see in the real world. The video signal may be determined by the computing system and communicated to the head mounted device 23. The device 23 can reproduce the received signal and the patient will thus see the real-life situation but in the virtual reality, which may be accompanied by an audio signal synchronised with the device. Because virtual reality systems respond to patient movements to create a sense of presence or "immersion"

within the virtual environment, the inventors have found that such systems provide an effective vehicle to treat a fear of the subject.

Various kinds of sensors and combinations of sensors can be used e.g. cameras can be used to determine the orientation of the head mounted device 23, and may also determine movements of e.g. body parts of the subject so that these movements can also be included in the video signal.

Such cameras may also be combined for example with accelerometers integrated in the head mounted device and/or accelerometers attached to the patient.

On the head mounted device 23, one or more objects are displayed and visualized. The objects visualized on the device may include a plurality of avatars which may be persons or animals. The objects may also include a virtual representation of physical objects. An avatar representing a subject may be included in a virtual situation or in a virtual scenario. After designing the objects that may be used in a given virtual environment, object characteristics may also be defined. These characteristics may contain rules of behaviour that define how a certain object may act or appear in a given environment. These dynamics are expressed through algorithms that may be embedded in a software.

Moreover, in some examples, a multisensory feedback may be provided. Said multisensory feedback signal may comprise a tactile feedback provided by a vibrator 27 in synchronization with e.g. a video signal. The vibrator 27 may be connected by cable or wirelessly with the controller 21. The controller may thus generate at a suitable moment a signal to active the vibrator 27. More than one vibrator may be used.

In this respect, when a vibration occurs to a virtual scenario due to a contact with a displayed avatar or by any object in the scene of the displayed script (in the case of vibrators located in body parts of the subject), the sense of "embodiment" and the results of the therapy season are enhanced.

There are a variety of ways in which such vibrating devices or alternative feedback devices may be used. In an example, if the script comprises a scene in which the subject touches or is being touched by a virtual object in the virtual reality, at the moment the avatar touches or is touched by the object, a tactile feedback may be created.

In some examples, the headphones 30 may be provided. The headphones 30 may again be connected to the controller 21 (either wireless or otherwise). Like the video images displayed on the head mounted device 23, an audio signal may be similarly provided to support the virtual environment illustrated in the head mounted device 23. Through the headphones 30, a patient may e.g. hear a speech related to the fear of the patient. Particularly, the speech may be aimed at overcoming such fear.

The volume of the sound emitted on headphones 30 may be also be adjusted. That is, in the virtual environment, the sound source may be assigned to a location. As the subject wearing the head mounted device moves his head, the sound volume may be slightly varied between the two speakers to coincide with the alignment of the subject's ears with the sound source.

In examples, a therapist may monitor and/or control the treatment of the subject via the computing system of the controller 21. In some other examples, the computing system may also be able to be run autonomously without anyone guiding it. The computing system may, for example, be a personal computer or a smartphone. As commented before, the computing system and the controller 21 may be in wired or wireless communication with one or more devices utilized by the subject to be treated including, for example, the head mounted device 23, the headphones 30, the tracking unit 24 or the vibrator 27.

Figure 2:
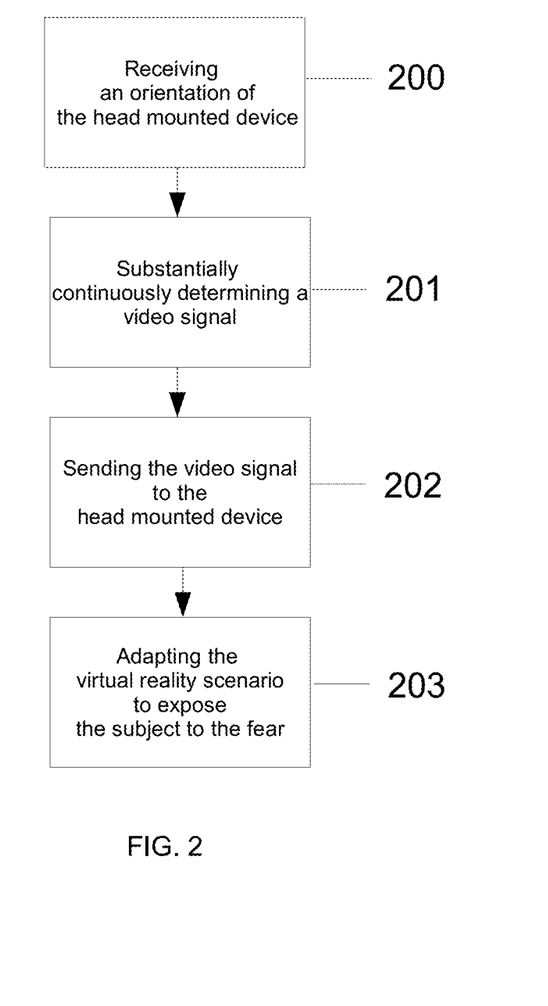
FIG. 2 illustrates a flow diagram of an example of a method for gradually exposing a subject to a fear.

Referring to FIG. 2, a flow diagram describing an example of a method for gradually exposing a subject to a fear is depicted, including the various steps of the method as processed by the controller.

At block 200, the above-commented controller may receive a subject's orientation from one or more sensors. As mentioned above, the subject's orientation is measured by one or more sensors comprised in a tracking unit which may in some examples be located on a head mounted device. Apart from the orientation of the HMD, also its position may be monitored and the position may be taken into account for the video signal to be generated. For example, if a subject moves his/her head forward or rearward without significantly affecting an HMD's orientation, the video signal to be reproduced may still be changed.

At block 201, a video signal is substantially continuously determined, the video signal including one or more objects in the virtual reality scenario to be displayed on the head mounted device taking into account the received orientation of the head mounted device. The controller may determine a video signal which represents a scenario. The scenario includes one or more objects e.g. one or more avatars, so that the objects may be displayed on the head mounted device in the selected scenario. At least some of the objects displayed in such scenario are arranged to provoke a particular fear in the subject to be treated.

There may be a wide variety of situations scripted which are basically configured to provoke a particular fear in a subject in combination with the objects displayed in such scenario.

A first scenario may be related to a "fear of heights". In cases in which the subject suffers from "fear of heights", the virtual environment may include one or more avatars standing at the same level e.g. on a virtual surface.

In other case falling within the second type of situations related to "fear of public speaking", the virtual environment may include a plurality of graphical presentations e.g. avatars, a floor over which the avatars may be situated, chairs which can be used by the avatars to have a seat and some other elements representing a realistic room or stage e.g. tables or some other environmental objects.

A further scenario might be created to subjects that have a fear of some specific animal. In cases in which the subject suffers from "fear of animals", the virtual environment may simply include a plurality of avatars and e.g. a floor over which the avatars may be situated. The avatars may be persons or animals. In examples, the script may further include some other elements representing a realistic natural environment (e.g. a jungle or a garden) in which the animal which provokes the fear usually lives.

It is noted that all the scripted situations may further include any simulated element which may be suitable to improve the virtual reality immersion.

In examples, the controller may further determine a video signal which represents an avatar of the subject i.e. the graphical representation of the subject undergoing the therapy, so that it may be also displayed on the head mounted device.

At block 202, the video signal may be sent to the head mounted device to be visualized. As the subject perceives a real-time correspondence between the images seen on the device and his/her head actual orientation in the environment, a sense of presence or "immersion" within the virtual environment is created.

In examples, as commented above, the video signal includes an avatar of the subject in the virtual reality scenario, the avatar of the subject performing the movements carried out by body parts of the subject. In this respect, as the subject perceives a real-time correspondence between the images seen on the display and his/her body's actual orientation in the environment, his/her brain is led to assume the virtual body as his/her own, that is, to experience the above-commented sense of ownership.

Thereafter, at block 203, the virtual reality scenario may be adapted to expose the subject to the fear by gradually transforming one or more of the objects from a first state to a second state, the second state of the object provoking an increase of the fear.

In the above-commented "fear of heights" situation, the subject may be listening to a central avatar, e.g. a virtual therapist attracting a center of gaze from the subject. The avatar may talk to the subject and he/she may help the subject with the "fear of height" issue by holding a monologue (or potentially a dialogue) about the fear, or about the virtual environment in which the avatar of the subject find himself/herself.

Further, the controller may determine whether one or more of the objects displayed in the head mounted device are in a peripheral field of vision of the virtual subject as derived from the orientation of the head mounted device.

Figure 3:
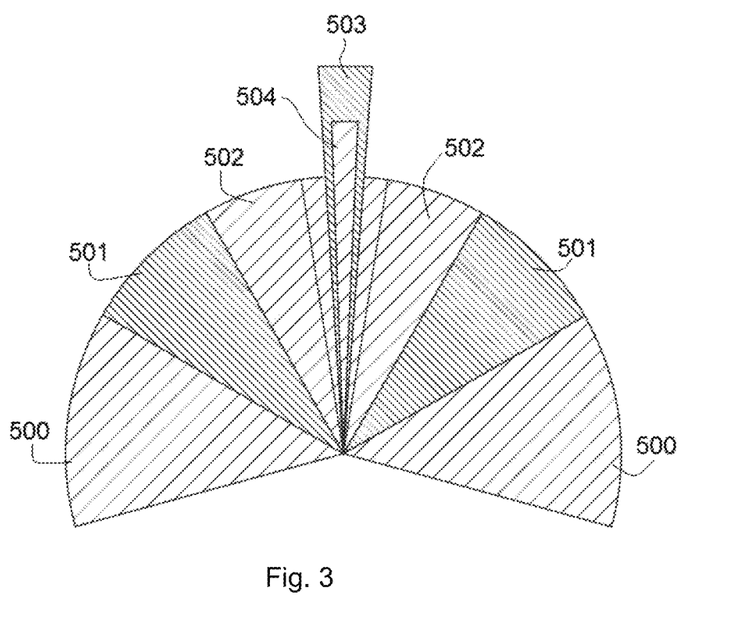
FIG. 3 illustrates an example of the peripheral vision of a human eye, FIGS. 4a-4h schematically illustrate a sequence of situations displayed on a head mounted device during an example of a treatment session.

As shown in FIG. 3, the peripheral field of view of the subject (as derived from the orientation of the head mounted device) may encompass the near peripheral field of view 502, the mid peripheral field of view 501 and the far peripheral field of view 500. The near peripheral field of view 502 may be defined as the field of vision deviating between e.g. 9 degrees and 30 degrees from a center of gaze (defined at 0 degrees) from the subject. The mid peripheral field of view 501 may be defined as the field of vision deviating e.g. between 31 degrees 60 degrees from the center of gaze from the subject. The far peripheral field of view 500 may be defined as the field of vision deviating e.g. between 61 and 100 or 110 degrees from the center of gaze from the subject.

Moreover, a paracentral field of view 503 may be defined as the field of vision deviating 8 or less degrees from the center of gaze of the subject. The paracentral field of view 503 may further encompass the central field of view 504 which may be defined as the field of vision deviating 5 or less degrees from the center of gaze of the subject.

In examples, the peripheral field of vision may be defined as the field of vision deviating more than 9° from a center of gaze from the subject (and thus the field of view, wherein the suitable avatars are transformed, encompasses the near peripheral field of view 502, the mid peripheral field of view 501 and the far peripheral field of view 500). However, in some other examples, the peripheral field of vision may be defined as the field of vision deviating at least 30° from the center of gaze of the subject. The peripheral field of view may thus only encompass the mid peripheral field of view 501 and the far peripheral field of view 500. In yet a further example, the peripheral field of view (suitable for performing a transformation of an avatar) may be only the mid peripheral field of view or even only the far peripheral field of view.

Before any change in the state of one or more objects is performed, the controller of the computer system may determine that a time condition has been fulfilled and that the object is located in the peripheral field of vision of the subject. If these conditions are given, the object(s) in question may transform into a second state. In the example of fear of heights, objects such as avatars or surroundings may move "downwards", or the avatar of the subject may move upwards. For example, one or more avatars and a group of houses virtually behind the avatars may be visualized. The avatars and the group of houses may be located in the peripheral field of vision of the subject. Over time, the video signal may be adapted to visualize the houses at the side of a slope such that a valley may be formed between the avatars and the houses. The avatars may move downwards in the valley, such that the avatars and the surroundings are in a second state, in which the avatars are lower than they were before. At this point, the virtual representation of the subject may look down onto the scenario. The avatar of the subject is now thus looking down from an increased height. It should be clear that this merely an example and that many other scenarios are possible. In order to ensure that the therapist is displaced downwards in a manner that is not very perceptible to the user, distractors may be used distracting the user while such a transformation takes place.

As commented above, the time condition may be either a variable amount of time depending on a perceived state of the subject or a predetermined amount of time i.e. not variable which has been previously set by e.g. a health care provider. In an example, a subject's heart rate, or respiratory rate or another parameter indicative of anxiety may be measured. And the time condition may be regarded as fulfilled as soon as the subject's parameters return to normal values. In yet a further example, a healthcare provider may provide input to the controller that according to his/her perception, the subject has calmed down enough to increase the exposure to fear.

Further transformations of the avatars or objects from one state to another may be performed in a substantially similar way. In this respect, over time, the avatars and surrounding located in a peripheral field of vision may get lower and lower, each time that the above-commented time condition is fulfilled. Eventually, the determined avatars located in the peripheral field of vision may disappear and a precipice may be virtually formed.

The anxiety causing situation i.e. the precipice may thus be gradually introduced in the subconscious mind of the subject while the subject does not notice it. Moreover, there is no sudden point when the subject is confronted with the precipice. Additionally, the avatar aimed at attracting a center of gaze from the subject may keep talking to the subject to allay the anxiety provoked.

In a scenario created for subjects suffering from a "fear of public speaking", the subject may be faced with a central avatar aimed at attracting a center of gaze from the subject. The avatar may help the subject with its fear, in this case, with the "fear of public speaking" issue. The avatar may again represent e.g. a human character of a therapist. And the central avatar may hold a monologue or engage in a dialogue with the avatar representing the subject with a fear.

Similarly as before, the controller may determine whether a time condition has been fulfilled. If so, in a peripheral field of vision, an avatar representing a further person (i.e. an audience) might appear. After a given time period, or at the control of the healthcare professional, or once the controller of the computing system determines that the subject's anxiety is below a given level, a similar transformation may take place. I.e. a further person may appear in the peripheral field of vision, or a cat or dog may transform into a person. Again, the audience for the subject suffering from a fear of public speaking is increased.

At the same time, at suitable moments, the persons located in a peripheral field of vision may move towards a center of gaze so that the subject becomes more aware.

If the time condition is fulfilled, the determined avatars which are displayed in the head mounted device in a peripheral field of vision of the subject are transformed from a first state to a second state, wherein the first state of the avatars may correspond to e.g. a more familiar avatar and the second state of the avatars may correspond to e.g. a more unfamiliar avatar Initially, each of the determined avatars may have the appearance of a completely familiar avatar (and this might be same avatar as the central avatar) so that the subject experiences a relaxed state associated with the feared object/situation. A gradual manipulation of the appearance of the determined avatars which are displayed in the head mounted device in a peripheral field of vision of the subject may be performed. The appearance of the avatars may comprise facial expression, body movement, posture, gestures, etc.

In a further example, one or more of the determined avatars which are displayed in the head mounted device in a peripheral field of vision of the subject as derived from the orientation of the head mounted device may be divided into two. Therefore, two identical copies of the avatars located in a peripheral field of vision of the subject may appear.

In a specific example, the central avatar may split up into two avatars, and one of them may move to a peripheral field of vision. Once a time condition has been fulfilled, and when the subject is not looking at that avatar, the avatar may transform into another avatar.

Further transformations of the determined avatars from one state to another may be performed in a substantially similar way. In this respect, as the time progresses (and thus more time conditions are fulfilled), the appearance of the avatars located in a peripheral field of vision of the subject may further be manipulated (and thus the appearance of the avatars may be more similar to a real unfamiliar avatar) and/or each of the avatars located in a peripheral field of vision of the subject may further be divided into two new avatars. In some examples, each of the avatars may further adopt a seated position.

The further avatars may further be gradually rendered as being attentive and/or interested. For example, the avatars located in a peripheral field of vision of the subject may gradually start to nod their heads in agreement with a point the subject under treatment is making. The avatars may also gradually start to laugh at an anecdote, gradually start to clap at appropriate times, and make good eye contact to indicate interest or engagement.

In any case, the gradual change in the appearance of the avatars and/or the gradual division of the avatars may predominantly take place in the peripheral vision. The splitting off commented on before may also take place in or close to the center of gaze. Since the split off will typically be from a familiar person/avatar, this does not necessarily increase anxiety.

The subject is thus confronted with unfamiliar members in the audience and/or new members in the audience in a gradual or subtle way. Moreover, the transformation of the avatars may take place imperceptibly, making use of change blindness. Therefore, there is no sudden moment when the subject is not speaking to a "familiar audience", and then is speaking to an "unfamiliar audience".

The inventors have found that that just as it is possible to speak to one familiar avatar without anxiety, the subject may find him or herself speaking to an unfamiliar avatar or an entire audience of unfamiliar avatars, since there has been an gradual transition to from "a single familiar avatar" to "an audience of unfamiliar avatars".

Yet another type of scenario may be created for subjects suffering from a "fear of animals" e.g. spiders. The avatar of the subject may be listening or looking at a central avatar. This might again be a person talking to the subject, but could take many different forms.

Surrounding the central avatar, there may be a plurality of persons or animals or objects.

Similarly as before, the controller may determine whether one or more of the surrounding objects are in a peripheral field of vision of the subject as derived from the orientation of the head mounted device.

Initially, the determined avatars may have the appearance of a familiar object e.g. a person or a cat so that the subject experiences a relaxed state associated with the feared object/situation.

Once the processor has determined the avatars which are displayed in the head mounted device in a peripheral field of vision of the subject as derived from the orientation of the head mounted device, the controller may further check whether a time condition is fulfilled. The time condition may be the same or similar as hereinbefore described.

If the time condition is fulfilled, one of persons may be gradually transformed from the above-commented initial state representing e.g. a familiar person to a second state. In the case of fear of spiders, the second state may correspond to a graphical representation of a spider. As the session continues, after given time periods, and for objects which are at those times located in the peripheral field of vision, further transformations may take placed. Further spiders might appear or a spider may take a scarier form.

It is noted that, in all the examples, the objects which are transformed from a first state to the second state may gradually be displaced towards the center of gaze as derived from the orientation of the head mounted device. This way, one more time, the anxiety causing situation is gradually introduce into the center of gaze of the subject. The subject is thus confronted with its fear in a gradual way.

It is further contemplated that examples of the present disclosure may be utilized to treat a subject having a wide variety of fear disorders e.g. agoraphobia, etc. . . . .

FIGS. 4a-4f schematically illustrate a sequence of situations displayed on a head mounted device, in an example, wherein a virtual reality scenario is created for subjects suffering from a "fear of public speaking". Same reference numbers denote the same elements.

Figure 4A:
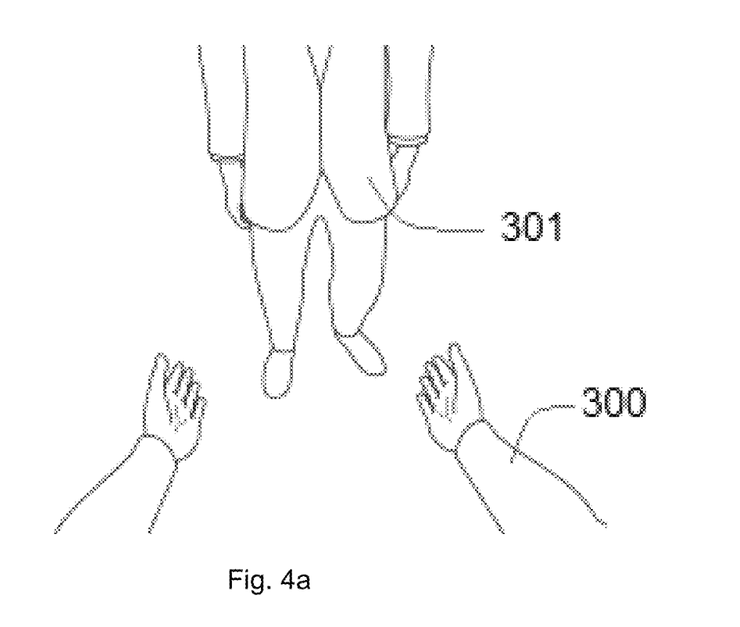

FIG. 4a illustrates an initial situation. In this initial situation, a subject may wear a head mounted device. A video signal may be sent to the head mounted device to be visualized. The video signal includes an avatar 300 of the subject in the virtual reality scenario, the avatar 300 of the subject performing the movements carried out by body parts of the subject. In this respect, as the subject perceives a real-time correspondence between the images seen on the display and his/her body's actual orientation in the environment, his/her brain is led to assume the virtual body as his/her own, that is, to experience a sense of ownership.

The video signal further includes a central avatar 301 attracting a center of gaze from the subject. In this example, the central avatar 301 may represent a human character of a therapist.

Figure 4B:
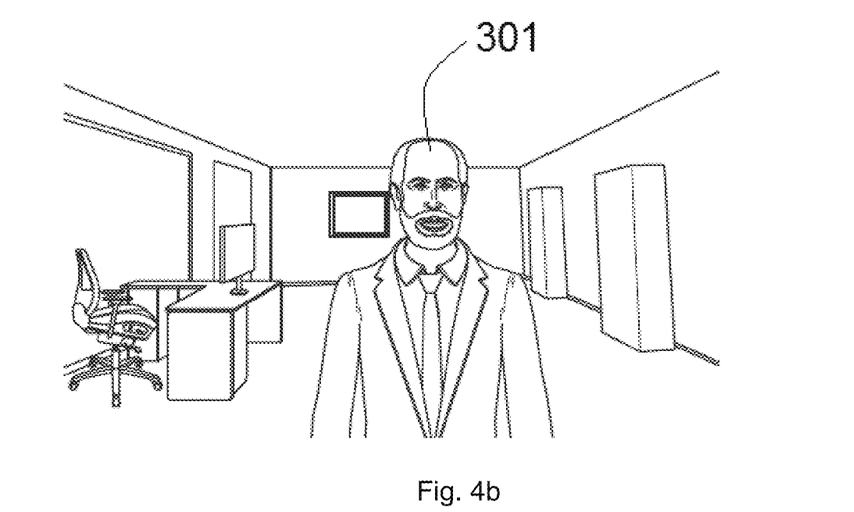

In FIG. 4b, the central avatar 301 may talk to the subject and he/she may help the subject with the "fear of public speaking" issue by holding a monologue (or potentially a dialogue) about the fear. Through headphones, the subject may hear a real or manipulated voice corresponding to the monologue held by the central avatar 301.

Figure 4C:
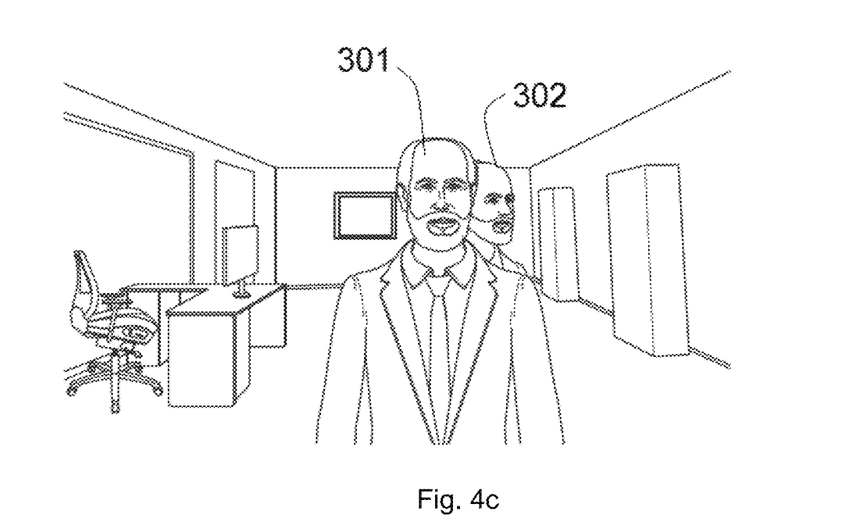
Figure 4D:
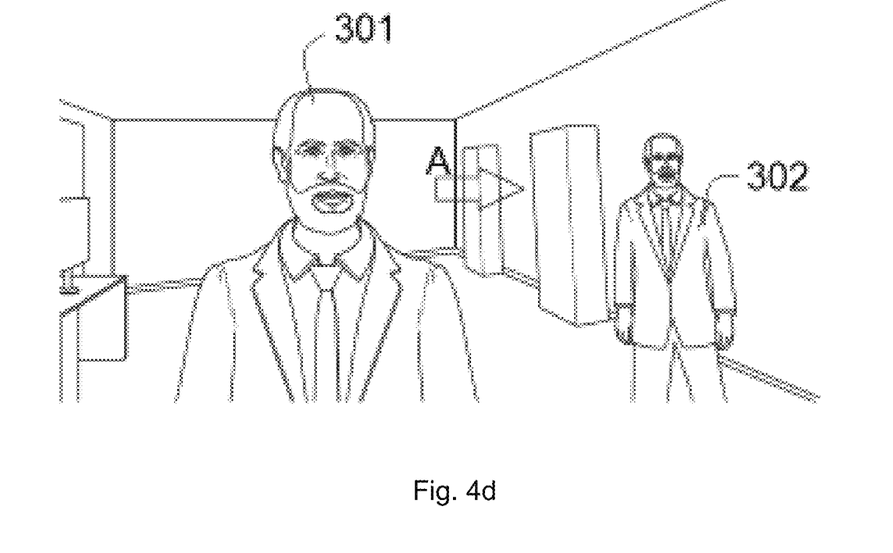

In FIG. 4c, the central avatar 301 may split up into two avatars 301, 302. This splitting off from the central avatar may be chosen not to increase the anxiety of the subject, i.e. if the central avatar is a familiar person, then the appearance of the same familiar person does not lead to a significant increase in anxiety. In FIG. 4d, the avatar 302 may move to a position corresponding to a peripheral field of vision of the subject in the direction of the arrow (arrow A).

Figure 4E:
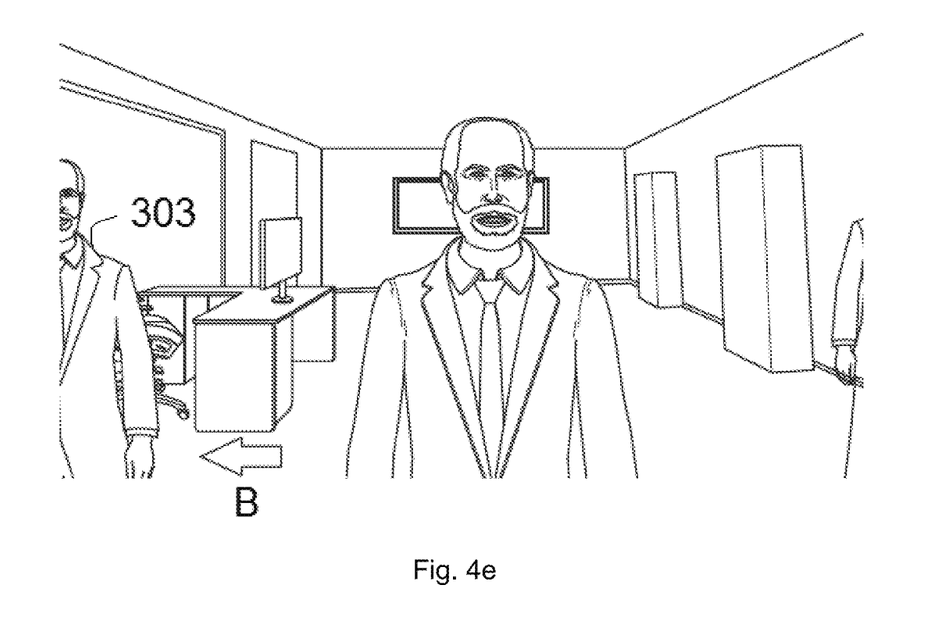

In FIG. 4e, similarly as before, the central avatar may have been split up in a further avatar 303. The avatar 303 may move to a position corresponding to the peripheral field of vision of the subject in the direction of the arrow (arrow B).

Figure 4F:
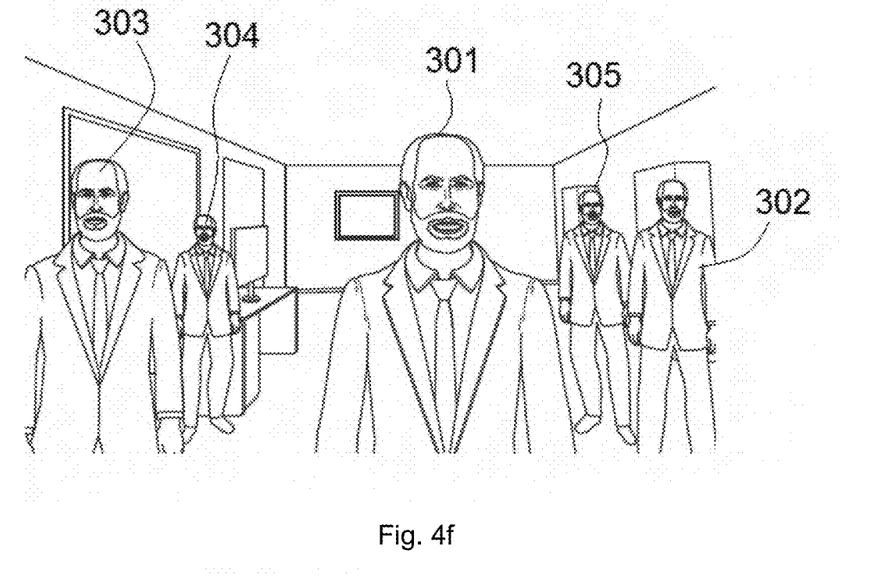

In FIG. 4f, the central avatar 301 has further been divided into two new avatars 304, 305 in a substantially similar way as hereinbefore described. It is noted that each of the avatars 302-305 may have the appearance of a completely familiar avatar (and this might be same avatar as the central avatar 301) so that the subject should be in a substantially relaxed state.

Figure 4G:
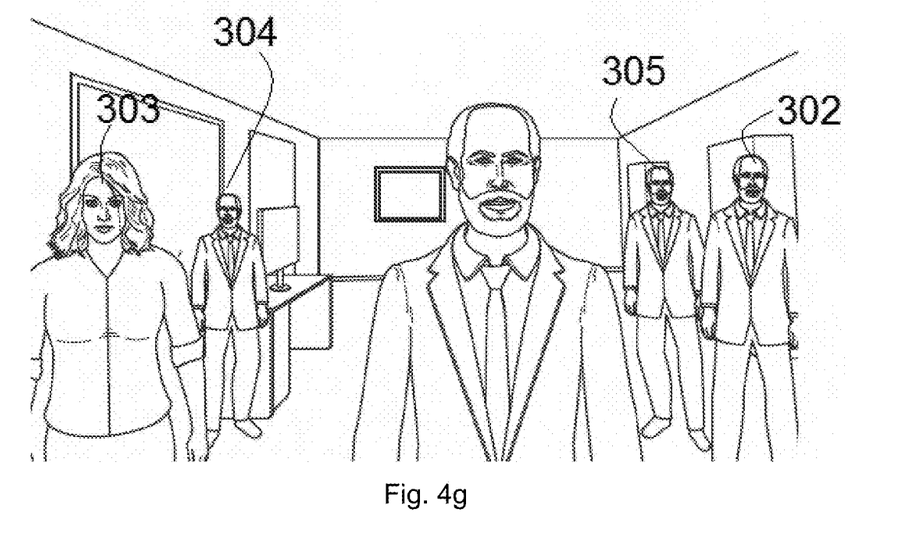

In FIG. 4g, the appearance of the avatar 303 located in a peripheral field of vision of the subject may be manipulated. The transformation may take place when the avatar 303 is in a peripheral field of vision. In this respect, the depicted appearance of the avatar may correspond to an unfamiliar avatar. As the time progresses, the appearance of the remaining avatars 302, 304, 305 may further be gradually manipulated in a similar way such that the appearance of the avatars 302, 304, 305 may correspond to further unfamiliar avatars (see FIG. 4h).

Figure 4H:
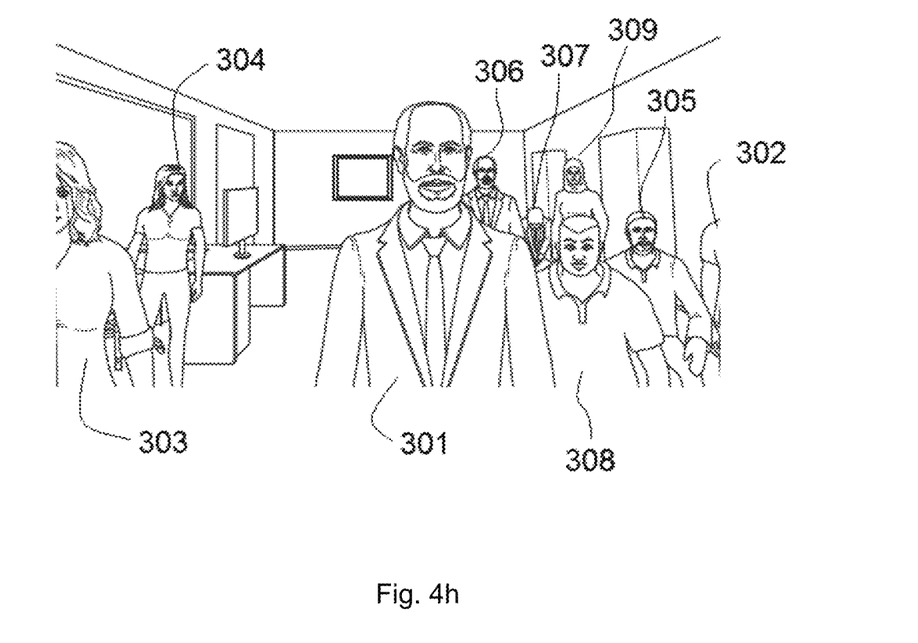

In FIG. 4h, the appearance of the avatars 302 (partially shown), 303, 304, 305 has already been manipulated such that the appearance of the avatars corresponds to unfamiliar avatars. The central avatar 301 may further be divided into new avatars 306-309 and the new avatars may be displaced to the peripheral vision of the patient in a substantially similar way as hereinbefore described. Moreover, the appearance of some of the avatars 308, 309 located in a peripheral field of vision of the subject has already been manipulated (and thus the appearance of the avatars may be more similar to an unfamiliar avatar). Moreover, some of the avatars 305, 307, 308 may further adopt a seated position.

As a result, the subject is confronted with unfamiliar members in the audience and new members in the audience in a gradual or subtle way. Moreover, the transformation of the avatars may take place imperceptibly, making use of change blindness. Therefore, there is no sudden moment when the subject is not speaking to a "familiar audience", and then is speaking to an "unfamiliar audience".

Figure 5A:
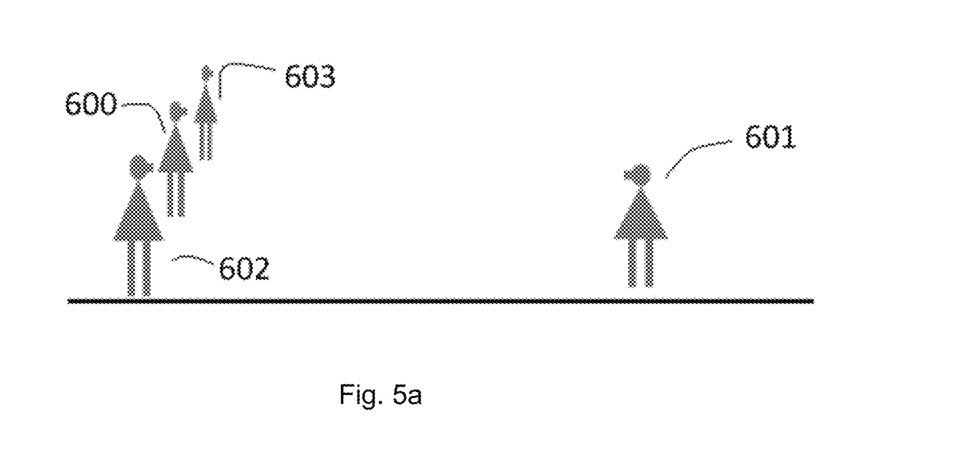
FIG. 5a-5c schematically illustrate a sequence of situations which may occur during a further example of a treatment session.
Figure 5B:
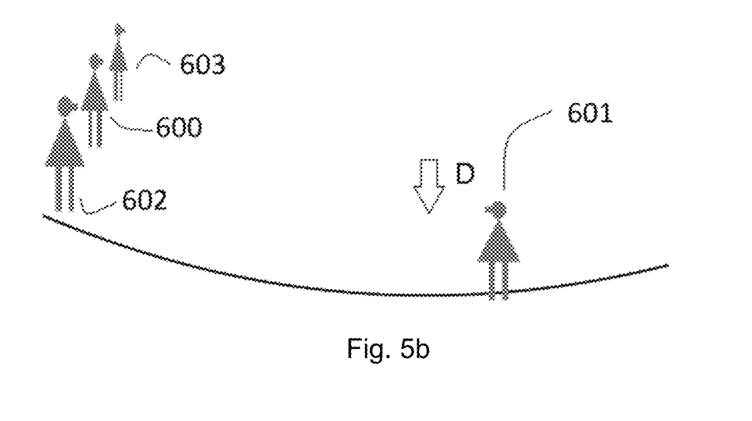
Figure 5C:
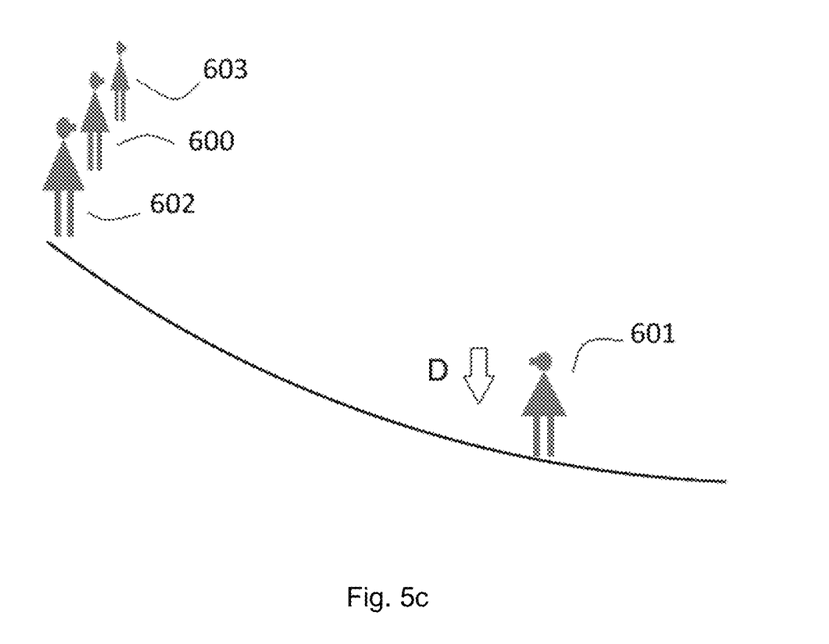

FIGS. 5a-5c schematically illustrate a sequence of situations which may occur during a treatment session, in an example, wherein a virtual reality scenario is created for subjects suffering from a "fear of heights". Same reference numbers denote the same elements.

A subject suffering from a fear of heights may wear a head mounted device with a display for reproducing a video signal received from a control system as in the other examples. The video signal includes a virtual reality scenario in which the subject may be represented by an avatar 500.

FIG. 5a illustrates an initial situation. The avatar 600 of the subject may be listening and talking to a central avatar 601, e.g. a virtual therapist. Additionally, some other avatars 602, 603 situated beside the avatar 600 of the subject may be visualized. The avatars 602, 603 may perform a function of "distractors" as will be explained later on. The central avatar 601, the avatar 600 of the subject and the avatars 602, 603 situated beside the subject may all be engaged in a multiway conversation. Through headphones, the subject may hear a real or manipulated voice corresponding to each of the avatars 601-603 involved in the conversation.

At some point, one of the avatars 602, 603 situated beside the avatar 600 of the subject may ask a question to the avatar 600 of the subject in order to attract a center of gaze from the subject. The subject may thus look at one of the avatars 602, 603 situated next to the subject 600. Other behaviour (different from asking a question) from one of the avatars may also attract the center of gaze from the subject. As the subject turns his/her head, the processor may determine that the central avatar 601 is displayed in the head mounted device in a peripheral field of vision of the subject as derived from the orientation of the head mounted device.

In FIG. 5b, the avatar of the subject 600 may keep talking to one of the avatars 602, 603 aimed at attracting a center of gaze from the subject and situated next to him/her. The controller may determine whether a time condition has been fulfilled. If so, the central avatar 601 which is located in a peripheral field of vision of the subject may be displaced a bit downwards in the direction of the arrow (arrow D) with e.g. a part of the floor so that the central avatar 601 may be on a different and slightly lower plane with respect to the remaining avatars.

In FIG. 5c, the conversation between the central avatar 601, the avatar 600 of the subject and the avatars 602, 603 may keep going. At some point, similarly as before, one of the avatars 602, 603 situated beside the avatar 600 of the subject may ask a question to the avatar 600 of the subject in order to attract a center of gaze from the subject. The subject may thus look at one of the avatars 602, 603 situated next to the subject 600. As result, the processor may determine that the central avatar 601 is displayed in the head mounted device in a peripheral field of vision of the subject as derived from the orientation of the head mounted device. At that moment, the central avatar and surroundings may be displaced virtually downwards again. A gradual exposure to the subject's fear may once again be established.

There are different ways of implementing the scenarios with distractors. A distraction may be carried only if a time condition has been fulfilled. Then, as soon as the subject changes his/her focus, a transformation may take place in a peripheral field of vision of the subject.

In another example, distractions may occur regularly or randomly and not be linked to a time condition. A transformation however will only take place whenever both the time conditions and the peripheral field of vision requirements are fulfilled.

Even though the use of "distractors" has only been explained in relation with the "fear of height" scenario, it should be clear that such distractors may also be used in any other virtual reality scenario that may be used. The use of the distractors may be useful in any of the scenarios to make sure that an object/avatar to be transformed will temporarily be in the peripheral field of vision. The appearance or activation of distractors may or may not be linked to the time condition.

For completeness, various aspects of the present disclosure have been set out in the following numbered clauses:

Clause 1. A method for gradually exposing a subject to a fear, the subject wearing a head mounted device for displaying a partially preprogrammed virtual reality scenario, the method comprising:

substantially continuously receiving from one or more sensors an orientation of the head mounted device of the subject;

substantially continuously determining a video signal including one or more objects in the virtual reality scenario to be displayed on the head mounted device taking into account the received orientation of the head mounted device;

sending the video signal to the head mounted device for visualization;

the method further comprising:

adapting the virtual reality scenario to expose the subject to the fear by gradually transforming one or more of the objects from a first state to a second state, the second state of the object provoking an increase of anxiety related to the fear; and wherein the transforming one or more of the objects takes place only if the following two conditions are fulfilled:

a time condition specifying an amount of time from the previous increase of fear, and the object is in a peripheral field of vision of the subject as derived from the orientation of the head mounted device.

Clause 2. The method according to clause 1, further comprising sending an audio signal to a device capable of reproducing the audio signal, wherein the audio signal when reproduced includes a voice talking about the fear of the subject.

Clause 3. The method according to clause 1 or 2, wherein the virtual scenario further comprises a central focus point aimed at attracting a center of gaze from the subject.

Clause 4. The method according to clause 3, wherein the central focus point is a central avatar talking to the subject.

Clause 5. The method according to any of clauses 1-4, wherein the virtual scenario further comprises a distractor aimed at temporarily attracting a center of gze from the subject.

Clause 6. The method according to clause 5, wherein activation of the distractor occurs after the time condition has been fulfilled.

Clause 7. The method according to any of clauses 1-6, wherein the peripheral field of vision is defined as the field of vision deviating more than 9° from a center of gaze from the subject.

Clause 8. The method according to clause 7, wherein the peripheral field of vision is defined as the field of vision deviating at least 30° from the center of gaze.

Clause 9. The method according to any of clauses 1-8, wherein the virtual reality scenario is adapted such that objects that have transformed to the second state are gradually moved towards the center of gaze as derived from the orientation of the head mounted device.

Clause 10. The method according to any of clauses 1-9, wherein the time condition is a predetermined amount of time since the previous increase of anxiety related to the fear.

Clause 11. The method according to any of clauses 1-9, wherein the time condition is a variable amount of time depending on a perceived state of the subject.

Clause 12. The method of clause 11, wherein the state of the subject is determined by measuring one or more physiological parameters.

Clause 13. The method of clause 12, wherein the physiological parameters include one or more of the following: respiratory rate, heart rate and perspiration.

Clause 14. The method according to any of clauses 1-13, wherein the virtual scenario includes the appearance of one or more objects in the first state.

Clause 15. The method according to any of clauses 1-14, wherein the objects are avatars.

Clause 16. The method according to any of clauses 1-15, further comprising continuously receiving from one or more sensors movements carried out by body parts of the subject, and wherein the video signal includes an avatar of the subject in the virtual reality scenario, the avatar of the subjecting performing the movements carried out by body parts of the subject.

Clause 17. The method according to any of clauses 1-16, wherein the fear is fear of public speaking, and the objects are avatars, wherein the first state of the avatars corresponds to a familiar avatar and the second state of the avatars corresponds to an unfamiliar avatar.

Clause 18. The method according to any of clauses 1-16, wherein the fear is a fear of an animal and the objects are avatars, wherein the first state of the avatars corresponds to a person, and the second state of the avatars corresponds to the animal.

Clause 19. The method according to any of clauses 1-16, wherein the fear is a fear of heights, wherein the first state of the objects corresponds to the objects as seen from a first height, and the second state of the objects correspond to the objects as seen from a second height.

Clause 20. A computer program comprising program instructions which when executed on a computer system cause the computer system to perform a method according to any of clauses 1-19.

Clause 21. A computing system comprising a memory and a processor, wherein computer program instructions executable by the processor are stored in the memory, the instructions comprising functionality to execute a method according to any of clauses 1-19.

Clause 22. A system for gradually exposing a subject to a fear comprising: a computing system according to claim 21;

a head-mounted device configured to reproduce the video signals received from the computing system;

one or more sensors configured to measure an orientation of a head mounted device of the subject.

Clause 23. A system according to clause 22, wherein the system further comprises headphones configured to reproduce the audio signal received from the computing system.

Clause 24. A system according to clause 22 or 23, wherein the one or more sensors comprise one or more of the following: accelerometers attached to the head mounted device, and video cameras.

Clause 25. A system according to any of clauses 22-24, further comprising one or more sensors for measuring physiological parameters of the subject.

Although only a number of examples have been disclosed herein, other alternatives, modifications, uses and/or equivalents thereof are possible. Furthermore, all possible combinations of the described examples are also covered. Thus, the scope of the present disclosure should not be limited by particular examples, but should be determined only by a fair reading of the claims that follow.

The invention claimed is:

1. A system for gradually exposing a subject to a fear, the system comprising:
a computing system comprising a processor and a memory storing computer program instructions executable by the processor;
a head-mounted device configured to reproduce video signals received from the computing system;

one or more orientation sensors configured to measure an orientation of the head mounted device when mounted on the subject; and one or more physiological sensors to measure one or more physiological parameters of the subject, the physiological parameters selected from the group consisting of respiratory rate, heart rate, and perspiration;

wherein the computer program instructions comprise functionality to:

substantially continuously receive from the one or more orientation sensors the orientation of the head mounted device of the subject, substantially continuously determine the video signals including one or more avatars in a virtual reality scenario to be displayed on the head mounted device taking into account the received orientation of the head mounted device, wherein the virtual reality scenario provides the subject with a feeling of being physically or perceptually within an environment, send the video signals to the head mounted device for visualization, and adapt the virtual reality scenario to expose the subject to the fear by gradually transforming one or more of the avatars from a first state to a second state, the second state of the one or more avatars to provoke an increase of anxiety related to the fear, the increase of anxiety being reflected by an output of the one or more physiological sensors, to expose the subject to an increased level of fear, wherein the virtual reality scenario further comprises a central focus point aimed at attracting a center of gaze from the subject, wherein the central focus point is a central avatar talking to the subject, and wherein the computer program instructions further comprise functionality to:

split the central avatar into a plurality of avatars, move one or more of the plurality of avatars to a peripheral field of vision, and wherein the transforming one or more of the avatars from a first state to a second state takes place responsive to the following:

a predetermined amount of time from a previous increase of anxiety related to the fear, as indicated by an output of the one or more physiological sensors, has passed, and the one or more of the avatars are in a peripheral field of vision of the subject as derived from the orientation of the head mounted device;

such that, responsive to passage of the predetermined amount of time, and responsive to the subject not looking at the one or more avatars moved to the peripheral field of vision, at least one of the one or more avatars transforms from the first state to the second state;

wherein repeated passage of the predetermined amount of time and transformation of additional ones of the one or more avatars from the first state to the second state exposes the subject to a gradually increased level of fear without necessarily provoking an increase in anxiety of the subject.

2. The computing system according to claim 1, wherein the peripheral field of vision is defined as the field of vision deviating more than 9° from a center of gaze from the subject.

3. The computing system according to claim 1, wherein the peripheral field of vision is defined as the field of vision deviating at least 30° from the center of gaze.

4. A system according to claim 1, wherein the system further comprises headphones configured to reproduce an audio signal received from the computing system, wherein the audio signal includes a voice talking about the subject's fear.

5. A system according to claim 1, further comprising sensors selected from the group consisting of accelerometers attached to the head mounted device, and video cameras.

6. A system according to claim 1, wherein the fear is selected from the group consisting of fear of public speaking, fear of heights, and fear of animals and wherein the first state of the avatars corresponds to an avatar familiar to the subject and the second state of the avatars corresponds to an avatar unfamiliar to the subject.

* * * * *